US009447017B2

(12) United States Patent
Bonrath et al.

(10) Patent No.: US 9,447,017 B2
(45) Date of Patent: Sep. 20, 2016

(54) PROCESS FOR THE PRODUCTION OF 4-ALKANOYLOXY-2-METHYLBUTANOIC ACID

(71) Applicant: DSM IP ASSETS B.V., Heerlen (NL)

(72) Inventors: Werner Bonrath, Basel (CH); Jan Schütz, Basel (CH); Bettina Wüstenberg, Basel (CH); Thomas Netscher, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/401,868

(22) PCT Filed: Jun. 5, 2013

(86) PCT No.: PCT/EP2013/061605
§ 371 (c)(1),
(2) Date: Nov. 18, 2014

(87) PCT Pub. No.: WO2013/182607
PCT Pub. Date: Dec. 12, 2013

(65) Prior Publication Data
US 2015/0099894 A1 Apr. 9, 2015

(30) Foreign Application Priority Data
Jun. 5, 2012 (EP) .................................... 12170781

(51) Int. Cl.
*C07D 311/00* (2006.01)
*C07C 69/66* (2006.01)
*C07C 67/29* (2006.01)
*C07C 29/15* (2006.01)
*C07C 45/00* (2006.01)
*C07D 311/72* (2006.01)

(52) U.S. Cl.
CPC ............... *C07C 67/29* (2013.01); *C07C 29/15* (2013.01); *C07C 45/008* (2013.01); *C07D 311/72* (2013.01)

(58) Field of Classification Search
CPC ....... C07C 69/16; C07C 69/29; C07C 29/15; C07C 45/608; C07D 311/72
USPC .......................................... 560/174; 549/408
See application file for complete search history.

(56) References Cited

U.S. PATENT DOCUMENTS 4,665,091 A 5/1987 Hoffman

OTHER PUBLICATIONS

Organic Chemistry 4e Carey, Chapter 17, Aldehydes and Ketones. Nucleophilic Addition to C=0 (2006).*
Organic Chemistry Portal, Recent literature (2003).*
Chinese Office Action issued in Application 201380029603.8 dated Jun. 30 2015.
Yi et al., Synthetic Perfume Technology, China Light Industries Press (Aug. 2007), pp. 209-210.
International Search Report for PCT/EP2013/061605, mailed Nov. 14, 2013, five pages.
Bassam et al., "Formic Acid-Palladium Acetate-1, 4-BIS (Diphenylphosphino) Butane: An Effective Catatalytic System for Regioselective Hydrocarboxylation of Simple and Functionalized Olefins", *Journal of Molecular Catalysis*, vol. 77, No. 1, Jan. 1, 1992, pp. 7-13.
Ohta et al., "Asymmetric Hydrogenation of Unsaturated Carboxylic Acids Catalyzed by BINAP-Ruthenium(II) Complexes", *Journal of Organic Chemistry*, vol. 52, No. 14, Jul. 10, 1987, pp. 3174-3176.

* cited by examiner

*Primary Examiner* — T. Victor Oh
(74) *Attorney, Agent, or Firm* — Nixon & Vanderhye P.C.

(57) ABSTRACT

The present invention relates to an improved process for the production of 4-alkanoyloxy-2-methylbutanoic acid, as well as to the use of such compounds in organic syntheses, especially in processes forming intermediates (building blocks) for the synthesis of organic compounds comprising isoprene (isoterpene) units, such as β-carotene or other carotenoids (e.g. canthaxanthin, zeaxanthin or astaxanthin) or as vitamin E or vitamin A as well as other structurally similar compounds.

17 Claims, No Drawings

PROCESS FOR THE PRODUCTION OF 4-ALKANOYLOXY-2-METHYLBUTANOIC ACID

This application is the U.S. national phase of International Application No. PCT/EP2013/061605 filed 5 June 2013 which designated the U.S. and claims priority to EP Patent Application No. 12170781.4 filed 5 June 2012, the entire contents of each of which are hereby incorporated by reference.

The present invention relates to an improved process for the production of 4-alkyloxy-2-methylbutanoic acid, as well as to the use of such compounds in organic syntheses, especially in processes forming intermediates (building blocks) for the synthesis of organic compounds comprising isoprene (=isoterpene) units, such as β-carotene or other carotenoids (e.g. canthaxanthin, zeaxanthin or astaxanthin) or as vitamin E or vitamin A as well as other structurally similar compounds.

Isoprene, which has the following chemical structure

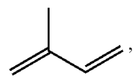

is an important chemical unit for a group of chemical compounds known as isoprenoids. Carotenoids as well as vitamin E as mentioned above are i.e. such isoprenoids.

Due to the importance of these compounds and the complexity of the synthesis thereof, there is always a need for improved processes of their production.

4-alkanoyloxy-2-methylbutanoic acid, the compound of formula (I)

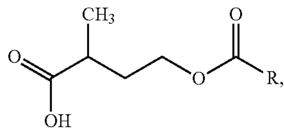

wherein R signifies a $C_1$-$C_{15}$ alkyl moiety or a $C_2$-$C_{18}$ alkenyl moiety, is an important compound (building block, starting compound) in such organic synthesis (for the production of isoprenoids).

When R is a $C_1$-$C_{15}$ alkyl moiety, then preferably the alkyl moiety is linear. Especially preferred alkyl moieties are methyl, ethyl and pentadecyl.

When R is a $C_2$-$C_{18}$ alkenyl moiety, there are one or more C-C double bonds. Preferably the alkenyl moiety is unbranched.

Compounds of formula (I) are known from the prior art, i.e. from Ali and Alper, J. Mol. Catal. 77 (1992), 7-13.

Described therein, there is also a process wherein a compound of formula (I) is obtained. But the therein disclosed and described process of production only allows to obtain compounds of formula (I) in low yield (12%) and in mixtures with other (main) products, so that the compounds of formula (I) have to be isolated.

The goal of the present invention was to provide an improved process of production of compounds of formula (I).

Surprisingly, it was found out that a compound of formula (I) can be obtained in an excellent yield by the following process

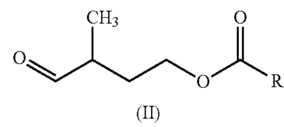

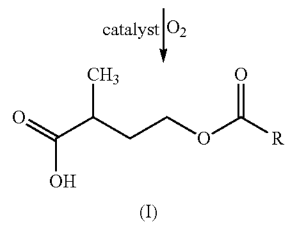

wherein R signifies a $C_1$-$C_{15}$ alkyl moiety or a $C_2$-$C_{18}$ alkenyl moiety, and when at least one transition metal salt is used as a catalyst in the oxidation process.

Therefore the present invention relates to a process of production of a compound of formula (I)

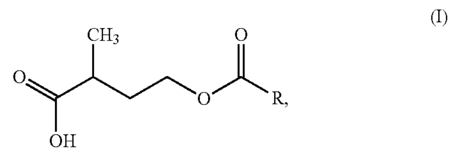

wherein R signifies a $C_1$-$C_{15}$ alkyl moiety or a $C_2$-$C_{18}$ alkenyl moiety, wherein a compound of formula (II)

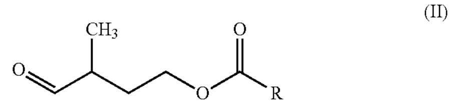

with R as defined as for compound of formula (I) is oxidised by using an oxygen-containing gas and characterised in that at least one transition metal salt is used as a catalyst.

Preferably, the present invention relates to a process of production of a compound of formula (I)

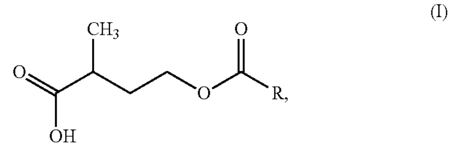

wherein R signifies a linear $C_1$-$C_{15}$ alkyl moiety (preferably methyl, ethyl and pentadecyl), wherein a compound of formula (II)

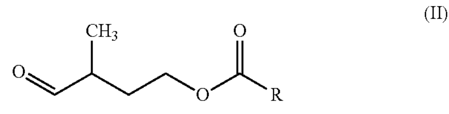

with R as defined as for compound of formula (I) is oxidised by using an oxygen-containing gas and characterised in that at least one transition metal salt is used as a catalyst.

In the context of the present patent application the term "transition metal" is defined as any element in the d-block of the periodic table, which includes groups 3 to 12 on the periodic table. The f-block is also (in the form of the lanthanide and actinide series) part of the definition.

The transition metal is the cation of the salt and the anion can be organic as well inorganic.

Preferred transition metals are Cu, Co, Fe and Cr.

The anion of the transition metal salt is not crucial for the invention. Any usually used anion can be the counterion. Preferred anions are halides (such as $Cl^-$, $Br^-$ or $I^-$), $PO_4^{3-}$, $SO_4^{2-}$ or $^-O(CO)CH_3$).

It is possible to use a single transition metal salt as well as mixtures thereof.

Preferred salts are $Co(O(CO)CH_3)_2$, $Cu(O(CO)CH_3)_2$, $CoSO_4$, $CuSO_4$, $Fe_2(SO_4)_3$, $CoCl_2$, $CuCl_2$ and $FeCl_3$.

Therefore the present invention relates to a preferred process of production of a compound of formula (I)

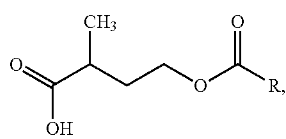

wherein R signifies a $C_1$-$C_{15}$ alkyl moiety or a $C_2$-$C_{18}$ alkenyl moiety, wherein a compound of formula (II)

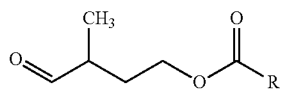

with R as defined as for compound of formula (I) is oxidised by using an oxygen-containing gas and characterised in that at least one transition metal salt selected from the group consisting of $Co(O(CO)CH_3)_2$, $Cu(O(CO)CH_3)_2$, $CoSO_4$, $CuSO_4$, $Fe_2(SO_4)_3$, $CoCl_2$, $CuCl_2$ and $FeCl_3$ is used as a catalyst.

Preferred compounds of formula (I) are

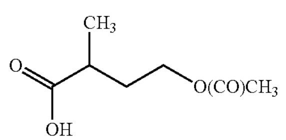

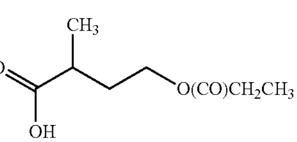

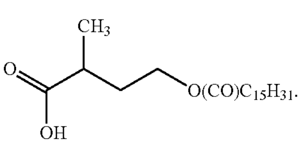

Therefore the present invention relates to a preferred process of production of a compound of formula (Ia)

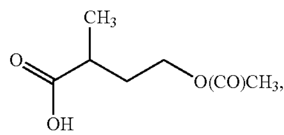

wherein a compound of formula (IIa)

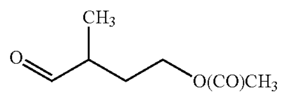

is oxidised by using an oxygen-containing gas and characterised in that at least one transition metal salt selected from the group consisting of $Co(O(CO)CH_3)_2$, $Cu(O(CO)CH_3)_2$, $CoSO_4$, $CuSO_4$, $Fe_2(SO_4)_3$, $CoCl_2$, $CuCl_2$ and $FeCl_3$ is used as a catalyst.

Therefore the present invention also relates to a preferred process of production of a compound of formula (Ib)

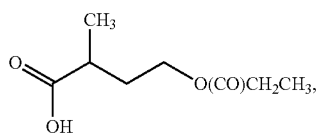

wherein a compound of formula (IIb)

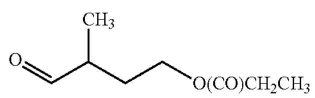

is oxidised by using an oxygen-containing gas and characterised in that at least one transition metal salt selected from the group consisting of $Co(O(CO)CH_3)_2$, $Cu(O(CO)CH_3)_2$, $CoSO_4$, $CuSO_4$, $Fe_2(SO_4)_3$, $CoCl_2$, $CuCl_2$ and $FeCl_3$ is used as a catalyst.

Therefore the present invention also relates to a preferred process of production of a compound of formula (Ic)

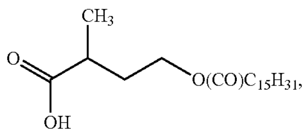

wherein a compound of formula (IIc)

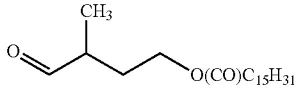

is oxidised by using an oxygen-containing gas and characterised in that at least one transition metal salt selected from the group consisting of $Co(O(CO)CH_3)_2$, $Cu(O(CO)CH_3)_2$, $CoSO_4$, $CuSO_4$, $Fe_2(SO_4)_3$, $CoCl_2$, $CuCl_2$ and $FeCl_3$ is used as a catalyst.

The process of the present invention is a catalytic oxidation. The oxidant used in the process is a gas comprising $O_2$. It can be pure $O_2$ gas as well as a mixture which comprises $O_2$ (such e.g. air).

Preferably the process according to the present invention is carried by using air as oxidant.

The process according to the present invention can be carried under pressure (up to 20 bar) as well as at ambient pressure.

Preferably the process according to the present invention is carried out ambient pressure.

The transition metal salt catalyst (as well as a mixture of such salts) is used in catalytic amounts.

Usually the transition metal salt catalyst (as well as a mixture of such salts) is used in an amount of 0.0005-0.1 mol equivalent (related to the mol of compound of formula (II)).

Therefore the present invention relates to a preferred process of production of a compound of formula (Ia)

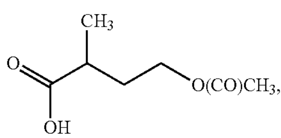

wherein a compound of formula (IIa)

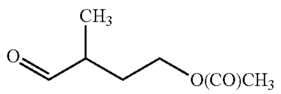

is oxidised by using an oxygen-containing gas and characterised in that 0.0005-0.1 mol equivalent (related to the mol of compound of formula (IIa)) of at least one transition metal salt selected from the group consisting of $Co(O(CO)CH_3)_2$, $Cu(O(CO)CH_3)_2$, $CoSO_4$, $CuSO_4$, $Fe_2(SO_4)_3$, $CoCl_2$, $CuCl_2$ and $FeCl_3$ is used as a catalyst.

Therefore the present invention also relates to a preferred process of production of a compound of formula (Ib)

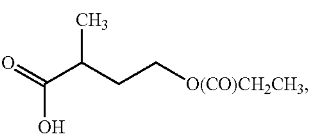

wherein a compound of formula (IIb)

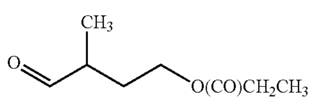

is oxidised by using an oxygen-containing gas and characterised in that 0.0005-0.1 mol equivalent (related to the mol of compound of formula (IIb)) of at least one transition metal salt selected from the group consisting of $Co(O(CO)CH_3)_2$, $Cu(O(CO)CH_3)_2$, $CoSO_4$, $CuSO_4$, $Fe_2(SO_4)_3$, $CoCl_2$, $CuCl_2$ and $FeCl_3$ is used as a catalyst.

Therefore the present invention also relates to a preferred process of production of a compound of formula (Ic)

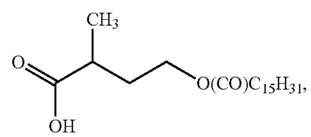

wherein a compound of formula (IIc)

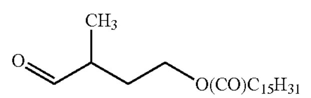

is oxidised by using an oxygen-containing gas and characterised in that 0.0005-0.1 mol equivalent (related to the mol of compound of formula (IIc)) of at least one transition metal salt selected from the group consisting of $Co(O(CO)CH_3)_2$, $Cu(O(CO)CH_3)_2$, $CoSO_4$, $CuSO_4$, $Fe_2(SO_4)_3$, $CoCl_2$, $CuCl_2$ and $FeCl_3$ is used as a catalyst.

The process according to present invention is usually carried out at temperatures of −10° C.-150° C., preferably 0° C.-80° C., more preferably 15° C.-70° C.

The process according to the present invention is usually carried out in a polar aprotic or polar protic solvent, as well as in mixtures of such solvents. Suitable solvents are esters (such as ethyl acetate), carbonates (such as ethylene carbonate), carboxylic acids (such as acetic acid, formic acid), alcohols (such methanol, ethanol, propanol, isopropanol), dimethylsulfoxide (DMSO), dimethylformamide (DMF), acetone, dichloroethane, dichloromethane and chloroform.

It is also possible that the process is carried out without any solvent.

The product of the process according to the present invention (compound of formula (I)) can be used in organic synthesis.

Usually the compound of formula (I) is used in the synthesis of an intermediate, which is then used for the synthesis of vitamin E, vitamin A or β-carotene, canthaxanthin, zeaxanthin or astaxanthin. Such process are known from the prior art.

The present examples serve to illustrate the present invention.

All parts given in the examples are related to weight and the temperatures are given in ° C., if not otherwise stated.

EXAMPLES

Example 1

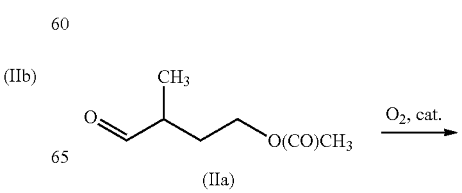

-continued

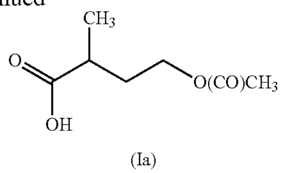

(Ia)

500 mg (3.34 mmol) of compound of formula (IIa) were dissolved in 10 ml of ethyl acetate (from Fluka).

8.0 mg (0.03 mmol =0.01 mol eq) of the catalyst Cu $(OAc)_2\times4\ H_2O$ (from Fluka) were added. The reaction mixture was heated to 40° C. and air was bubbled through the solution for 20 h. The reaction mixture was washed with water (2×15 ml) and the combined aqueous phases were extracted with ethyl acetate (2×25 ml). The combined organic phases were dried over sodium sulfate, filtered, and concentrated in vacuo (45° C., 200 to 20 mbar). A liquid was obtained which comprised the compound of formula (Ia) in 87.3% yield.

Example 2

500 mg (3.34 mmol) of compound of formula (IIa) were dissolved in 10 ml of ethyl acetate (from Fluka).

9.0 mg (0.03 mmol=0.01 mol eq) of the catalyst Co $(SO_4)_2\times5\ H_2O$ (from Sigma) were added. The reaction mixture was heated to 40° C. and air was bubbled through the solution for 20 h. The reaction mixture was washed with water (1×20 ml, 1×10 ml) and saturated NaCl solution (10 ml). The combined aqueous phases were extracted with ethyl acetate (2×10 ml). The combined organic phases were dried over sodium sulfate, filtered, and concentrated in vacuo (45° C., 300 to 10 mbar). The product was obtained as a liquid in 59% yield.

Example 3

500 mg (3.34 mmol) of compound of formula (IIa) were dissolved in 10 ml of ethyl acetate (from Fluka).

0.6 mg (0.003 mmol) of the catalyst $CuCl_2\times2\ H_2O$ (from Acros) were added. The reaction mixture was heated to 40° C. and air was bubbled through the solution for 3 h. All volatiles were removed in vacuo (45° C., 180 to 20 mbar). The product was obtained as a liquid in 83% yield.

Example 4

Comparative Example 500 mg (3.34 mmol) of compound of formula (IIa) were dissolved in 10 ml of ethyl acetate (from Fluka).

36 mg (0.03 mmol=0.01 mol eq) of the catalyst Pd/C (10%) were added. The reaction mixture was heated to 40° C. and air was bubbled through the solution for 17 h. All volatiles were removed in vacuo (45° C., 180 to 20 mbar). The product was obtained as a liquid in 45% yield.

From example 4 it can be seen that another (commonly used) catalyst does not lead to the yields that were achieved with the process as described and claimed by the present patent application.

The invention claimed is:

1. A process for producing a compound of formula (I):

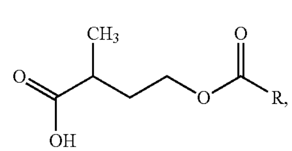

(I)

wherein R signifies a $C_1$-$C_{15}$ alkyl moiety or a $C_2$-$C_{18}$ alkenyl moiety, wherein the process comprises oxidizing a compound of formula (II):

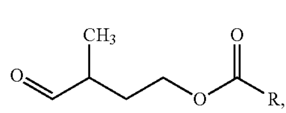

(II)

wherein R in formula (II) is the same as defined for the compound of formula (I), in an oxygen-containing gas and in the presence of at least one transition metal salt as a catalyst.

2. The process according to claim 1, wherein the transition metal of the transition metal salt is selected from the group consisting of Cu, Co, Fe and Cr.

3. The process according to claim 1, wherein the anion of the transition metal salt is selected from the group consisting of halides, $PO_4^{3-}$, $SO_4^{2-}$ and $O(CO)CH_3$.

4. The process according to claim 1, wherein the transition metal is selected from the group consisting of $Co(O(CO)CH_3)_2$, $Cu(O(CO)CH_3)_2$, $CoSO_4$, $CuSO_4$, $Fe_2(SO_4)_3$, $CoCl_2$, $CuCl_2$ and $FeCl_3$.

5. The process according to claim 1, wherein R in formula (I) and in formula (II) is a linear alkyl moiety.

6. The process according to claim 1, wherein the oxygen-containing gas is $O_2$ gas or air.

7. The process according to claim 1, wherein the process is carried out under a pressure up to 20 bar or at ambient pressure.

8. The process according to claim 1, wherein the at least one transition metal salt catalyst is present in an amount of 0.0005-0.1 mol equivalent relative to one mol of the compound of formula (II).

9. The process according to claim 1, wherein the process is carried out at a temperature of −10° C.-150° C.

10. The process according to claim 1, wherein the process is carried out in a polar aprotic or polar protic solvent.

11. The process according to claim 1, wherein the process is carried out in the absence of solvent.

12. The process according to claim 1, wherein the anion of the transition metal salt is a halide anion selected from the group consisting of $Cl^-$, $Br^-$ and $I^-$.

13. The process according to claim 5, wherein the linear alkyl moiety is selected from the group consisting of methyl, ethyl and pentadecyl.

14. The process according to claim 9, wherein the process is carried out at a temperature of 0° C.-80° C.

15. The process according to claim 9, wherein the process is carried out at a temperature of 15° C.-70° C.

16. The process according to claim 10, wherein the solvent is at least one selected from the group consisting of esters, carbonates, carboxylic acids, alcohols, dimethylsulfoxide (DMSO), dimethylformamide (DMF), acetone, dichloroethane, dichloromethane and chloroform.

17. The process according to claim 16, wherein the solvent is at least one selected from the group consisting of ethyl acetate, ethylene carbonate, acetic acid, formic acid, methanol, ethanol, propanol and isopropanol.

* * * * *